United States Patent [19]

Silverstein et al.

[11] Patent Number: 5,193,525

[45] Date of Patent: Mar. 16, 1993

[54] ANTIGLARE TIP IN A SHEATH FOR AN ENDOSCOPE

[75] Inventors: Fred E. Silverstein, Seattle, Wash.; Eric A. Opie, deceased, late of Brier, Wash., by Elizabeth J. O. Salamonsen, Executrix; David R. Kreft, Seattle, Wash.; Bandula Wijay, Friendswood, Tex.

[73] Assignee: Vision Sciences, Natick, Mass.

[21] Appl. No.: 620,488

[22] Filed: Nov. 30, 1990

[51] Int. Cl.$^5$ ............................................. A61B 1/00
[52] U.S. Cl. ...................................................... 128/4
[58] Field of Search ................. 128/4, 6, 7, 8; 358/98; 604/263

[56] References Cited

U.S. PATENT DOCUMENTS

| | | | |
|---|---|---|---|
| 4,419,987 | 12/1983 | Ogiu | 128/6 X |
| 4,622,954 | 11/1986 | Arakawa et al. | 128/6 |
| 4,646,722 | 3/1987 | Silverstein et al. | 128/4 |
| 4,677,471 | 6/1987 | Takamura et al. | 128/6 X |
| 4,721,097 | 1/1988 | D'Amelio | 128/4 |
| 4,788,967 | 12/1988 | Ueda | 128/6 |
| 4,794,911 | 1/1989 | Okada | 128/4 |
| 4,805,598 | 2/1989 | Ueda | 128/6 |
| 4,974,580 | 12/1990 | Anapliotis | 128/4 |

FOREIGN PATENT DOCUMENTS

| | | |
|---|---|---|
| 61-179128 | 8/1986 | Japan . |
| 63-33209 | 9/1988 | Japan . |
| 2-33120 | 2/1990 | Japan . |
| 2-132409 | 5/1990 | Japan . |

Primary Examiner—Gene Mancene
Assistant Examiner—Thomas Price
Attorney, Agent, or Firm—Seed and Berry

[57] ABSTRACT

An antiglare tip for the sheath of an endoscope to prevent glare in an image viewer is disclosed. The antiglare tip includes an interfitting region with the endoscope to ensure that all light entering the image viewer is reflected from objects external to the endoscope. An opaque projection extends from the endoscope insertion tube between the light source and the image viewer. Opaque recesses in the tip are positioned to mate with the opaque projections extending from the endoscope end. Having mating projections and recesses aligned ensures that no light may pass directly from the light source to the image viewer via the tip. Glare resulting from internal reflections in the tip, or from an inside surface of the tip, is prevented.

31 Claims, 11 Drawing Sheets

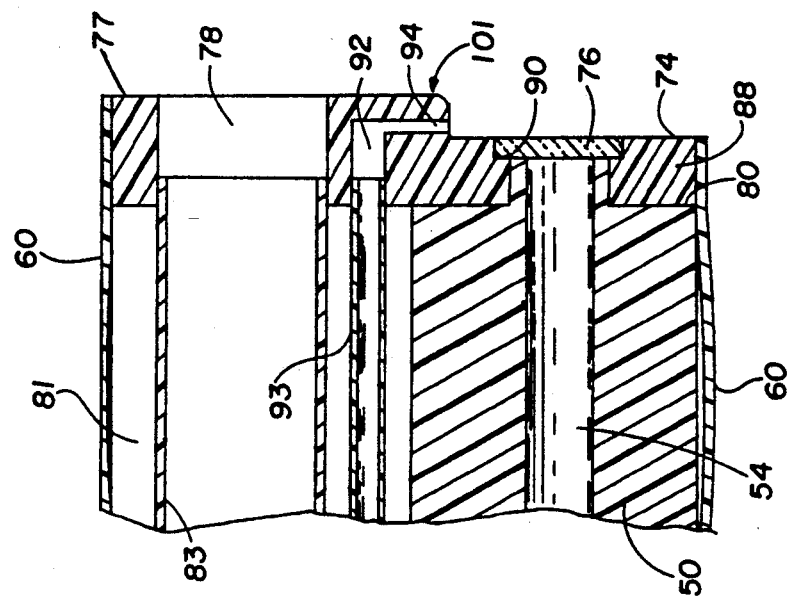
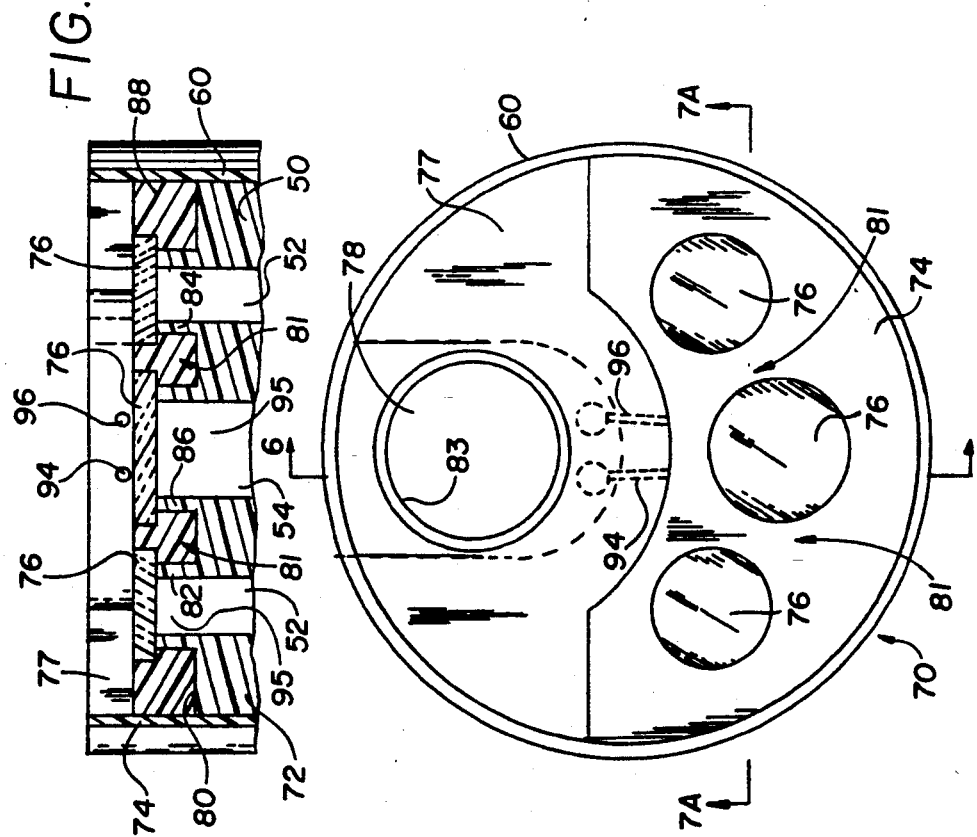

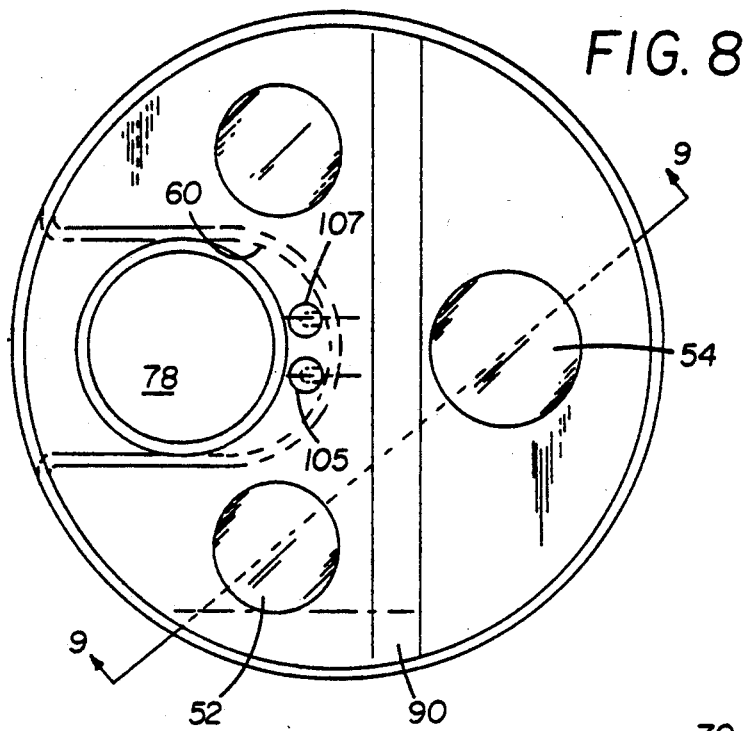
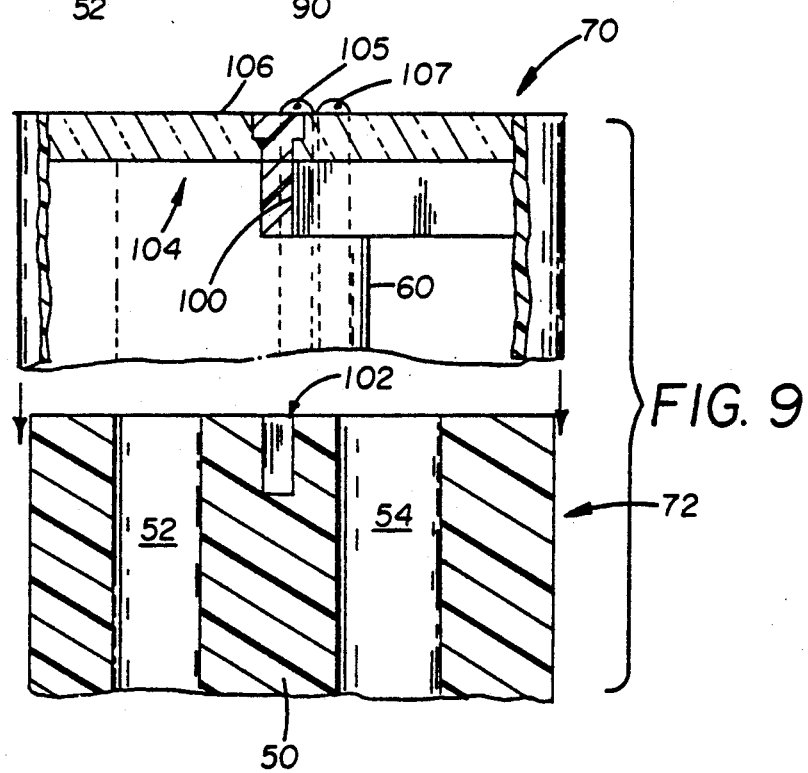

ANTIGLARE TIP IN A SHEATH FOR AN ENDOSCOPE

DESCRIPTION

1. Technical Field

This invention relates to endoscopes, and more particularly, to an antiglare tip for ensuring that only light reflected from objects external to the endoscope enters the image viewer.

2. Background of the Invention

Endoscopes are presently used in the medical and industrial fields. Within the medical field, endoscopes have many uses. Frequently the endoscope design and name are based on its use. For example, there are upper endoscopes for examination of the esophagus, stomach and duodenum, cystoscopes for examining the bladder, colonoscopes for examining the colon, angioscopes for examining the blood vessels and heart, bronchoscopes for examining the bronchi, laparoscopes for examining the peritoneal cavity, arthroscopes for examining joint spaces, and sigmoidoscopes for examining the rectum and sigmoid colon. Industrial endoscopes, sometimes called boroscopes, may be used for examining contaminated or inaccessible locations, such as the interior of large vessels used for nuclear reactors and similar environments.

Endoscopes extend a user's vision and access into places the user cannot enter directly. For example, cavities within the human body are generally sufficiently small to prevent direct vision and access without surgery. Similarly, a person cannot enter the inside of a nuclear reactor without receiving deadly doses of radiation. Accordingly, endoscopes are provided for examining and probing environments which a person may not enter directly.

To illuminate and provide a view of objects, endoscopes are generally provided with an image viewer and one or more light sources. The light sources emit a bright light to illuminate external objects so that they can be viewed through the image viewer. The user is then able to perform the desired task, such as medical diagnosis, treatment, or the like.

Enclosing an endoscope insertion tube in a sheath to prevent contamination is described in U.S. Pat. No. 4,646,722, to Silverstein et al., which is incorporated herein by reference. A sterilized sheath having a transparent window at its distal end is placed over the endoscope insertion tube prior to each use. Unfortunately, the transparent window can potentially create glare in the image.

Glare is created by the transparent window in many different ways. Light emitting from the light guide may reflect from an inside surface of the window and into the image viewer. Alternatively, light may reflect within the window itself and enter the image viewer, creating a ghost image or glare. This glare interferes with the ability of the user to view a coherent and sharp image. Preferably, only light reflected from objects external to the endoscope should be permitted to enter the image viewer, so that the view provided to the user represents a true image.

Numerous unsuccessful attempts have been made to eliminate glare occurring in sheaths around endoscopes. Japanese Utility Publication No. 63-33209, to Yamamoto and assigned to Olympus Optical, describes a protrusion extending from the end of the endoscope to hold the sheath away from contact with the light-emitting and image viewer lenses. Glare is not prevented because light entering the sheath from the light sources may be reflected internally to the image viewer, creating a ghost image or glare. U.S. Pat. No. 4,794,911, to Okada, describes a cap mounted on the distal end of an endoscope. The light sources are flush with the end of the endoscope. Glare occurs because light is reflected from the inside surface of the cap and enters the image viewer. Direct light from the light source enters the image viewer, preventing a clear view of external objects. One reason that sheaths have not been widely used on endoscopes is because of the difficulty of obtaining an image which contains only light reflected from external objects and is free from unwanted glare.

SUMMARY OF THE INVENTION

According to principles of the invention, there is an interfitting region between a sheath tip and an endoscope, positioned between the light source and the image viewer, to prevent glare in the image viewer. The interfitting region includes a projection from the endoscope mating with a recess in the sheath tip. Alternatively, the projection may extend from the sheath tip and mate with a recess in the endoscope. The interfitting region includes a light-blocking member to ensure that only light reflected from objects external to the endoscope may enter the image viewer.

According to one embodiment of the invention, an endoscope insertion tube has opaque projections around the light source and image viewer. The sheath tip includes opaque recesses aligned for mating with the projection from the endoscope. The projections extending into the sheath tip and mating with respective recesses in the tip ensures that light cannot pass directly from the light source to the image viewer. The biopsy channel extends from an aperture in a raised step of the tip. Water and air channels extend perpendicular from the raised step and are aligned with the image viewer to ensure adequate cleaning.

The tip is preferably manufactured by forming apertures within a single-piece opaque member and mounting lenses in the apertures. The lenses are mounted flush with the top surface of the single-piece opaque member to provide a flat surface which is easy to keep clean. The apertures form the recesses that mate with the projections of the endoscope. The endoscope tip may thus be easily mass-produced and reliably manufactured using mechanized techniques.

According to alternative embodiments of the invention, either the light source or the image viewer protrude from the end of the endoscope and the other is flush with a top surface of the endoscope. Alternatively, both may protrude or both may be flush with a top surface. In all embodiments, an interfitting region includes a light-blocking member that extends between the light source and the image viewer to ensure that no light passes directly from the light source to the image viewer.

BRIEF DESCRIPTION OF THE DRAWINGS

FIG. 5 is an end plan view of a sheath tip and endoscope combination of FIG. 3.

FIG. 6 is a cross-sectional view taken along lines 6—6 of FIG. 5.

FIG. 7A is a cross-sectional view taken along lines 7A—7A of FIG. 5.

FIG. 8 is an end plan view of an alternative embodiment of a sheath tip and endoscope combination having an opaque projection extending into the endoscope.

FIG. 9 is an exploded cross-sectional view taken along lines 9—9 of FIG. 8.

DETAILED DESCRIPTION OF THE INVENTION

Figure 1:
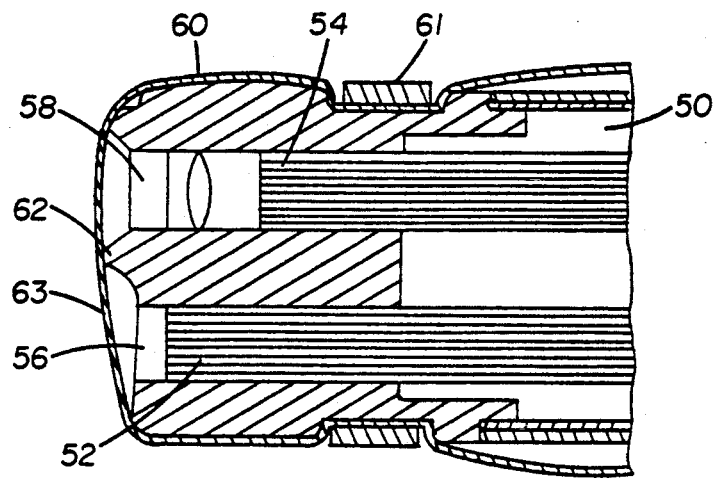
FIG. 1. is a cross-sectional view of a prior art glare prevention device for a sheathed endoscope.

FIG. 1 illustrates a prior art structure from Japanese Utility Publication No. 63-33209 for reducing glare caused by an endoscope sheath. A prior art endoscope 50 includes a light source 52 and an image viewer 54. Lenses 56 and 58 are positioned over the light source 52 and the image viewer 54, respectively. A sheath 60 extends over the end of the endoscope 50, covering the lenses 56 and 58. A band 61 holds the sheath 60 on the endoscope 50. An opaque protrusion 62 extends between the light source 52 and the image viewer 54. The opaque protrusion 62 is designed to prevent the direct transmission of light to the image viewer 54 from the light source 52.

Unfortunately, opaque protrusion 62 does not effectively prevent light from passing directly to the image viewer 54 from the light source 52, and glare results. In practice, the sheath 60 may become slightly separated from the opaque protrusion 62, leaving a gap between the sheath 60 and the opaque protrusion 62. Light exiting from lens 56 reflects from the inside surface of the sheath 60, passes through the gap, and enters the lens 58, causing significant glare. Internal reflections within the sheath 60 itself are a second source of glare. Some of the light entering the inside surface of the sheath 60 is also reflected internally from the outside surface 63 of sheath 60. This reflected light remains within the sheath layer stretched over the end of the endoscope, and is reflected to the image viewer 54. This internally reflected light within the sheath 60 creates a ghost image, halo, or glare that interferes with the user viewing a coherent image. A further problem is that the band 61 may be pulled off and lost within a human body, causing additional problems such as intestinal obstruction or pulmonary aspiration. Accordingly, this prior art fails to solve the problem of glare caused by light entering the image viewer 54 directly from the light guide 52, without first being reflected by external objects.

Figure 2:
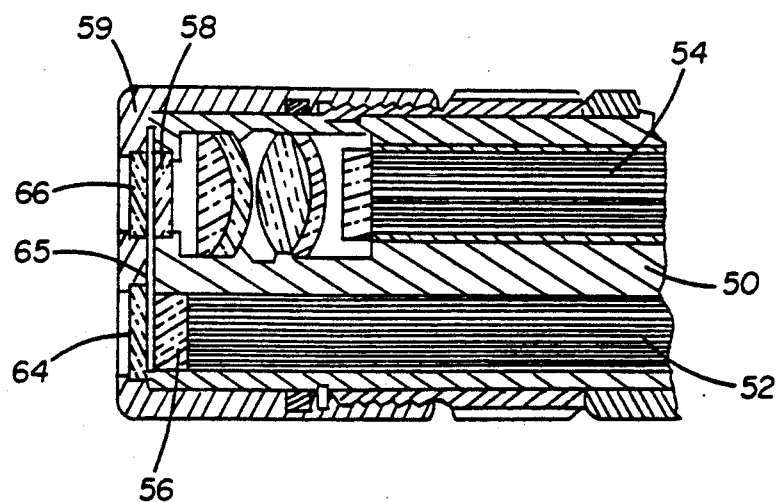
FIG. 2 is a cross-sectional view of a prior art sheath tip.

FIG. 2 illustrates a different prior art endoscope 50 having a tip 59, as shown in U.S. Pat. No. 4,794,911. The endoscope 50 includes a light guide 52 and an image viewer 54, similar to that shown in the prior art of FIG. 1. A light source lens 56 and a viewer lens 58 are mounted flush with the surface of the endoscope 50. Tip lenses 64 and 66 are mounted flush with an inside surface of the tip 59. Some of the light exiting from light source 52 reflects from the inside surface 65 of the lens 64, creating glare in image viewer 54. A second problem is that debris may enter the recess around the lenses and be difficult to remove, further blocking a clear view.

Figure 3:
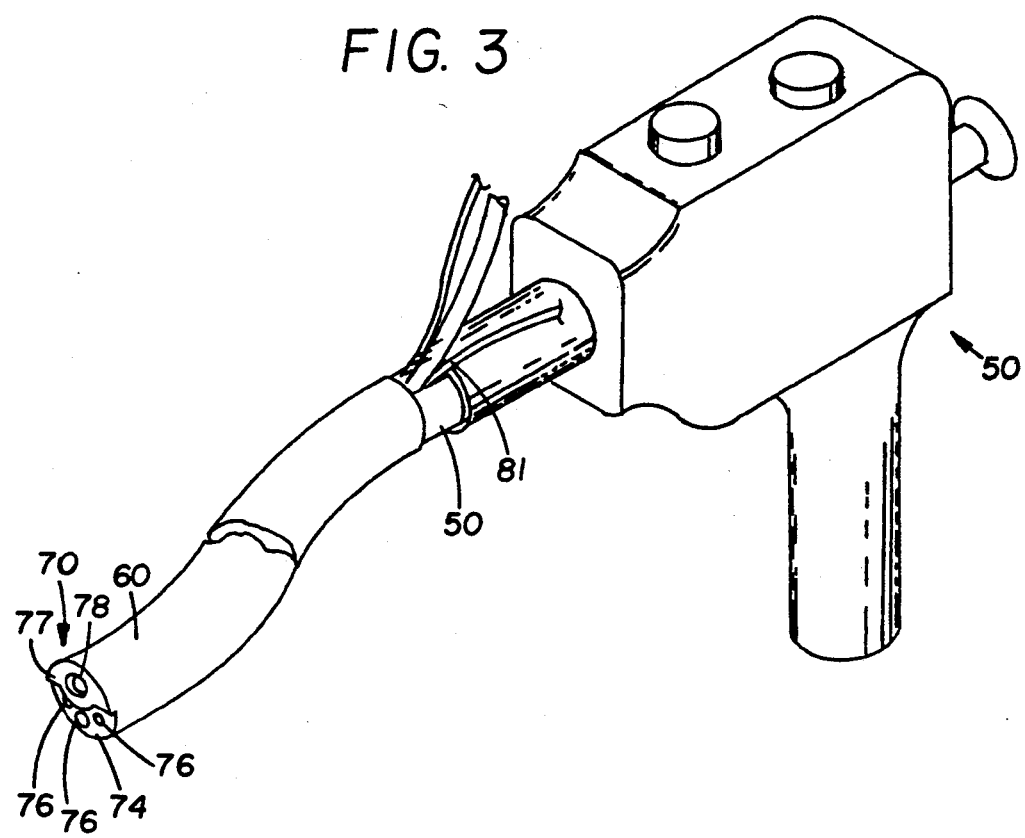
FIG. 3 is an isometric view of an endoscope having a sheath extending around the insertion tube.

FIG. 3 illustrates the inventive antiglare tip 70 on a sheath 60 covering an endoscope 50. The endoscope 50 and sheath 60 may be of the type described in U.S. Pat. No. 4,646,722 or any other suitable prior art sheath and endoscope combination, such as those shown in FIGS. 1 and 2. However, according to principles of the invention, the structure at the distal end 72 of the endoscope is configured to cooperate with the tip 70 of the sheath 60 to provide an interfitting region that prevents glare in the image viewer, as explained in more detail herein.

Figure 4:
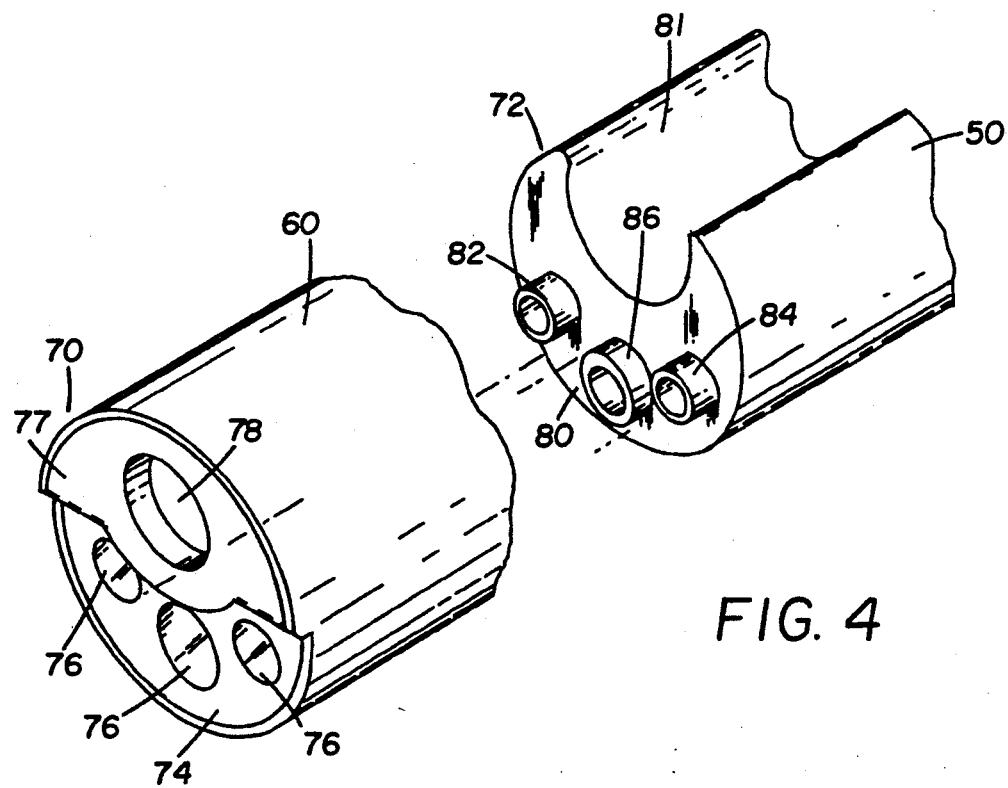
FIG. 4 is an exploded isometric view of the endoscope and sheath tip combination of FIG. 3.

FIG. 4 illustrates a sheath 60 having the inventive tip 70 positioned for extending over the distal end 72 of endoscope 50. The tip 70 includes an outside surface 74 having lenses 76 located therein and positioned to mate with corresponding light sources and an image viewer in end 72 of endoscope 50. The lenses 76 may be any suitable light transparent member, including flat lenses, concave, convex, light-gathering lenses, or of other types generally known in the art, such as those shown in FIGS. 1 and 2. The lenses 76 are mounted with their edges flush with outside surface 74, providing a smooth and continuous outside surface across tip 70. If lenses 76 are concave or convex, the edges are mounted flush with the outside surface 74, and any deviations from the flat surface 74 occur in the smooth continuous shape of the lens. This precludes tip surface recesses, or sharp protrusions, which can accommodate debris, are difficult to wash off, and can interfere with the image.

A raised step 77 includes an aperture 78 for aligning with the suction or biopsy channel of the endoscope. The aperture 78 and interface of the biopsy channel of the endoscope is made by any conventional method known in the art, such as that described in U.S. Pat. No.

4,947,827, incorporated herein by reference and having the same inventive entity. Having the biopsy channel in a raised step on the tip 70 is not required, and this portion may be flat with surface 74; however, the raised section facilitates cleaning of the lenses with wash and air sprays, as explained later.

The end 72 of endoscope 50 includes a flat surface 80 and projecting portions 82, 84, and 86. The projecting portions extend above the flat surface 80 of end 72 and surround the light sources and image viewer. A groove 81 is provided for receiving a removable biopsy tube and air and water tubes as is known in the art from those patents incorporated by reference.

In use, the sheath 60 is placed over the insertion tube of endoscope 50 and the tip 70 is brought into abutting contact with end 72. The user inserts the sheath endoscope, having the antiglare tip 72 thereon, into the patient's body under examination, or, for an industrial endoscope, into the vessel to be examined. After use, the endoscope is removed from the patient, the sheath 60, together with tip 70, is removed from the endoscope 50 and disposed of in the appropriate manner to prevent the spread of contamination from the sheath.

FIGS. 5, 6, 7A, 7B and 7C provide an enlarged and detailed view of the inventive tip 70 and end 72 of endoscope 50. An interfitting region 81 of the sheath tip 70 and the endoscope 50 includes light-blocking members positioned between the light source and the image viewer to prevent glare. Opaque projections 82, 84, and 86 of the endoscope 50 mate with opaque recesses 95 of the tip 70 to form the interfitting region 81 on an inside surface of the tip 70.

The tip 70 includes a single-piece opaque member 88 having a flat outside surface 74 and a raised step 77. The lenses 76 are positioned in apertures within the single-piece opaque member 88. A hole is formed by any acceptable method, such as drilling, punching, injection molding having the appropriate hole therein, or the like, to provide the apertures. The apertures are countersunk, that is, contain an enlarged diameter portion having a shoulder 90. The depth of the enlarged diameter portion providing shoulder 90 is selected to equal the height of the edges of lens 76, so that when the lens 76 abuts against the shoulder 90, the top surface, at the edges, is flush with flat outside surface 74 of the tip 70. Having the aperture countersunk with the shoulder 90 increases manufacturing speed by permitting the lens 76 to be press fit into the aperture until it solidly abuts the shoulder 90 while ensuring the proper mounting of lens 76. The lens 76 may be secured in the aperture by any suitable technique, such as press fitting, gluing at the edges, or the like.

The opaque member 88 extends in an interfitting relationship between the light source and the image viewer to ensure that all possible paths of light are blocked. Even if the end piece 88 is not in abutting contact or correct alignment with the end 72, reflected light can be prevented from entering the image viewer 54 because the projections 82, 84, and 86 extend in a direction perpendicular to the direction of light travel between the light guide 52 and the image viewer 54. The sheath 60 may stretch, twist, or be distorted during use, especially within the inside of a patient separating the opaque member 88 from the endoscope end 72. Light is still reliably blocked from directly entering the image viewer via the tip because the opaque member 88 extends longitudinally towards the endoscope in a direction perpendicular to the path the light must travel to create the unwanted glare. Preferably, the opaque member 88 surrounds either the light guide 52 or image viewer 54, or both, to block all light from entering the image viewer 54 which is not reflected from objects outside of the endoscope.

As illustrated in FIG. 6, the raised step 77 is configured to cooperate with groove 81 of endoscope 50, having a biopsy channel 83 therein. The raised step 77 includes a large aperture 78 coupled to the biopsy or suction channel 83 of the endoscope. The raised step 77 also includes one or more through channels 92 having a high-pressure nozzle 94. The channels 92 are in fluid communication with tubes supplied by the endoscope to provide water and air at the outside of the tip. A water supply tube 93 is coupled to channel 92 having a nozzle 94 formed therein. The nozzle 94 provides a wash jet at the appropriate pressure to wash the outside surface of lens 76. Similarly, an air supply tube 97 (see FIG. 7B) is coupled to an air nozzle 96 to provide an air jet at the appropriate pressure.

The sheath 60 and tip 70 completely seal the endoscope 50 from the outside environment and possible contamination. The sheath 60 is coupled to the tip 70 and, in one embodiment, extends between the water tubing 93, air tubing 97, biopsy channel 83 and the endoscope 50 (see FIG. 7B). In an alternative embodiment, the sheath surrounds the endoscope but does not extend around the tubings 93 and 97, the tubings being completely sealed to contain contamination. The sheath 60 also completely surrounds the endoscope 50. The sheath 60, biopsy channel 83, water tubing 93, and air tubing 97 are coupled to the tip 70 by any suitable method, including adhesives, plastic welding, heat fusing, or other suitable technique that forms a contamination barrier.

As shown in FIG. 6, the nozzles 94 and 96 are an integral part of the single-piece opaque member 88. The nozzles 94 and 96 extend perpendicular to the flat outside surface 74 of the tip 70. The nozzles 94 and 96 are formed by drilling into the stepped portion 77 at the desired height to provide the appropriate diameter for a nozzle for the wash and air channels. The nozzles 94 and 96 are drilled to a sufficient depth to mate with the recess extending in from the inside surface of the opaque member 88 to form the channel 92. Having the wash nozzle 94 and air nozzle 96 extend perpendicular to and point across one or more lenses 76 provides the advantage that the lens may be completely and reliably cleaned as needed.

Manufacturing costs are saved and the reliability enhanced by the construction of nozzles 94 and 96 as an integral part of the one-piece member 88. Forming the nozzle 94 as an integral part of the opaque member 88 significantly decreases manufacturing costs because they may be easily formed and the mounting of nozzles avoided. The raised step 77 provides a convenient location for integrally mounting the nozzles adjacent the lenses 76, one of the advantages of raised step 77. Having the nozzles 94 mounted in the raised step 77 also increases their reliability because they are recessed and protected by the raised step 77, thus preventing them from being broken or damaged when the endoscope is in use. Patient comfort is also enhanced because the raised step 70 may be constructed in a smooth, rounded shape as shown at corners 101 and does not have external extending nozzles, which have the possibility of irritating an inside surface of the patient's body.

The tip 70 may be constructed by any suitable method. For example, a preferred material for the single-piece opaque member 88 is a black plastic disk. The disk is machined to provide flat outside surface 74, raised step 77, and the appropriate apertures and channels, as described. The apertures and nozzles are formed by common techniques, such as drilling, punching, or the like. Alternatively, the opaque member 88 may be injection-molded having the desired shape and thus be mass-produced having the raised step 77, flat surface 74, and the appropriate apertures preformed in the injection mold. Any other suitable technique for providing the tip 70 of suitable opaque material having the structure as shown, may also be used.

As shown in FIG. 7A, interfitting region 81 includes projections 82, 84, and 86 mating with single-piece member 88, seen in cross section. The projections 82, 84, and 86 are opaque members that extend above the surface 80 of the endoscope. These projections mate with the recesses 95 of the tip 72, as previously explained, to form the interfitting region 81 that prevents light from passing from the light source 52 to the image viewer 54.

Figure 7B:
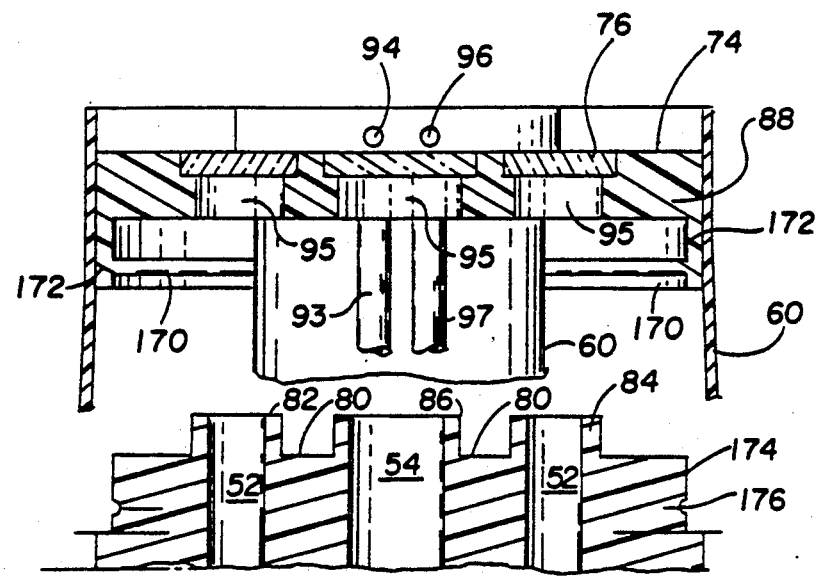
FIG. 7B is an exploded cross-sectional view of an alternative embodiment of a sheath tip and endoscope combination.

With the lens 76 mounted therein, the aperture forms a recess 95, as best seen in FIGS. 7A and 7B. The single-piece opaque member 88 forms the sidewalls of the recess 95, and the lens 76 is sealed into the opaque member 88 to ensure that contamination and matter cannot pass to the endoscope 50 from outside of the sheath 60. The depth of the sidewalls of recess 95 are selected based on the height of projections 82, 84 and 86 to ensure that the inside surface of opaque member 88 abuts against the flat surface 80 of end 72 prior to the lens 76 striking any projection. Having the opaque member 88 abut against the surface 80 ensures that all light exiting from the light guide 52 is blocked by the tip except that portion exiting from the appropriate lens 76 and also prevents the lens from being dislodged by the endoscope.

FIG. 7B illustrates an alternative embodiment having a locking snap mechanism to hold the tip 70 onto the endoscope 50. The tip 70 includes a protrusion 170 extending from the inside surface of a shoulder 172. The endoscope 50 includes an indent 176 within a recess 174 positioned to mate with the protrusion 170 and shoulder 172, respectively. The shoulder 172 deflects slightly to permit the protrusion 170 to slide along an inside surface of the recess 174 and snap into the indent 176. The shoulder 172 and protrusion 170 are sufficiently resilient to grip the endoscope 50 and hold the tip 70 in position on the endoscope throughout the medical procedure. At the conclusion of the procedure, the tip snaps off of the endoscope and is removed, together with the sheath. The shoulder 172 preferably extends for at least a short distance circumferentially around the tip 70 so that if the tip twists, the protrusion 170 remains within the indent 176. In one embodiment, the shoulder 172 extends completely around the tip 70 to form a ring to ensure that the tip 70 does not separate from the endoscope 50 unless it is intentionally removed at the conclusion of a procedure.

Figure 7C:
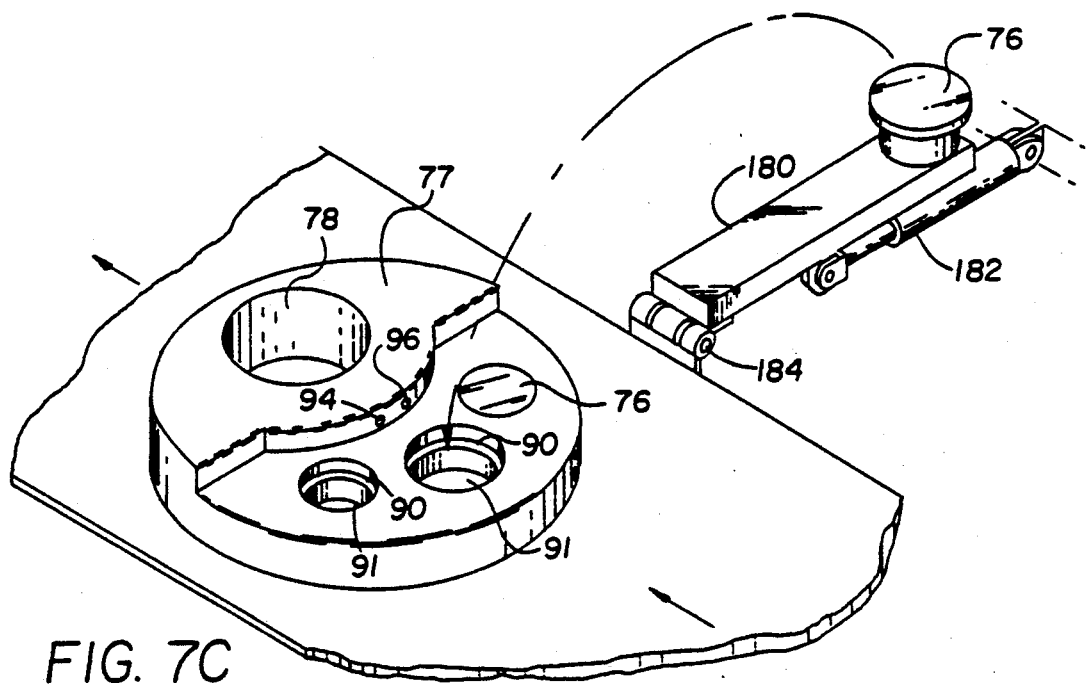
FIG. 7C is an isometric view of a mechanical apparatus useful in one step of manufacturing the tip.

FIG. 7C illustrates a mechanical arm 180 for inserting lenses 76 into the tip 70 during one step of the manufacturing process. A lens 76 is held in cup 186. The lens 76 is held by any suitable mechanism, such as a suction cup, as shown, fingers gripping at its edges or the like. Adhesive may be applied to the edges of the lens 76 prior to inserting it into the tip 70. The arm 180 pivots about pivot 184 under control of actuator 182. As the arm pivots downward, the lens 76 is inserted into the tip 70 and press fit into solid abutment with shoulder 90 to form a flush top outside surface, as previously described. The arm 180 then pivots back to the initial position, receives a new lens 76, and pivots forward to place the new lens 76 into the correct aperture 91 of the tip 70. The tip 70 and/or the arm 180 are appropriately moved between insertion operations to position the proper aperture 91 in alignment to receive the lens using mechanized assembly techniques known in the art. The next tip 70 is then advanced into position for the inserting of lenses 76.

Alternatively, the lenses 76 may be manually mounted using similar techniques. The lens 76 may be held in the hand of a worker, adhesive applied, if desired, and pressed, by hand, into the appropriate aperture 91 until it abuts against shoulder 90. The tip 70 may thus be manually manufactured if desired. In both embodiments of manufacture, mechanical and manual, the lenses 76 form a tight seal with the tip 70 to ensure that contaminated matter may not seep through the tip and contact the endoscope 50.

The appropriate lenses, waveguides, and fiberoptic members may be used as part of the light source and image viewer as is well known in the prior art. The terms "light source" and "image viewer" are broadly defined to include their full assembly within an endoscope. For example, the light source includes not only the source of the light and light guide if used, but also the lenses and windows within the endoscope that facilitate the illumination of objects extending to the endoscope. Similarly, the image viewer includes the CCD imager or fiberoptic cable as well as the light collecting and focusing lenses, windows, and the like that provide an image, or signal representing an image, from the distal end of the endoscope to a proximal end of the endoscope.

In summary, the technical advantages of the antiglare tip and endoscope combination are that light is prevented from passing from the light source directly to the image viewer by a recess of the endoscope tip 70 mating with a projection extending from the endoscope. Opaque member 88 within the tip itself blocks light, preventing it from spreading directly from the light source 52 to the image viewer 54 through the lens material. The opaque member 88 solidly abuts against the end of the endoscope to ensure that light reflected from an inside surface of the lens 76 is blocked and may not enter the image viewer 54.

Advantages in manufacture are provided by constructing the opaque blocking member 88 from a single piece. Having the bores for the lenses 76 countersunk increases the manufacturing speed and ensures that the edge surfaces reliably register with the upper surface 74 to provide a smooth, flat interface between the edge of the lens and the surface 74.

FIGS. 8 and 9 illustrate an alternative embodiment of an interfitting region 81 having a projection 100 mating with recess 102 in the end of endoscope 50. The majority of the tip 70 is clear, being formed of a transparent material. Lenses or, alternatively, a plastic transparent member functioning merely as a clear cover may be used as tip 70.

The projection 100 extends between the light source 52 and the image viewer 54, providing an opaque barrier. The opaque projection 100 extends completely through the tip 70 from an outside surface 106 to an inside surface 104, and then projects beyond the surface 104. The position and shape of opaque barrier 100 ensures that light cannot travel through the lens material itself from the light source 52 to the image viewer 54.

The projection 100 extends longitudinally into the recess 102 within the endoscope 50, ensuring that any light reflected from the inside surface 104 of the tip 70 is blocked and cannot be received by the image viewer 54. The opaque projection 100 extends perpendicular to the direction light must travel to pass directly from the light source 52 to the image viewer 54. Even if the tip 70 separates slightly from the surface 72, light is still blocked by the longitudinally-extending opaque member 100.

An aperture 78 is provided in the tip 70 for the biopsy channel as previously described with respect to FIGS. 3-7 or using some other structure which may be available in the art. In this embodiment, the entire surface of the tip 70 is flat, the biopsy aperture 78 being flush with the surface of the tip and not in a raised step. The wash and air channels extend from small nozzles 105 and 107, respectively, adjacent the biopsy tubing, according to a manner known in the art to provide the needed wash and dry functions.

The embodiment of FIGS. 8 and 9 may also be constructed from a single-piece opaque disk 88 by mounting lenses 76 at the appropriate locations and having multiple projections 100, similar to that shown and described in FIGS. 3-7. If a single-piece disk 8B is used, the lenses are mounted flush with a top surface. Recesses are formed in the endoscope end 72 in place of one or more of the projections 82, 84, and 86 so that a projection 100 extending from the tip 70 mates with and enters into a corresponding recess of endoscope end 72. The projections and recesses of the tip and the end 72 are reversed from those shown in FIGS. 3-7.

Figure 10:
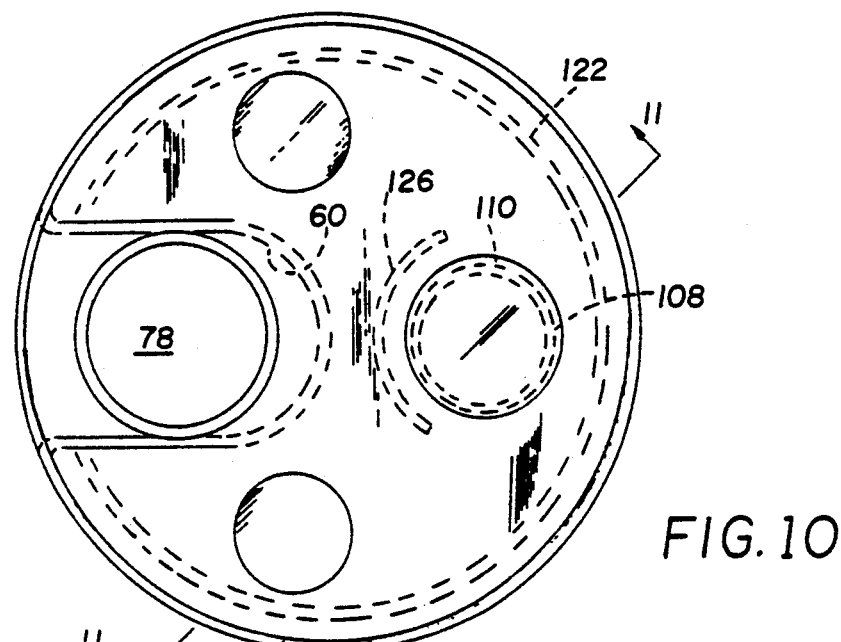
FIG. 10 is an end plan view of an alternative embodiment of a sheath tip and endoscope combination having a projection from the endoscope extending into the sheath tip.
Figure 11:
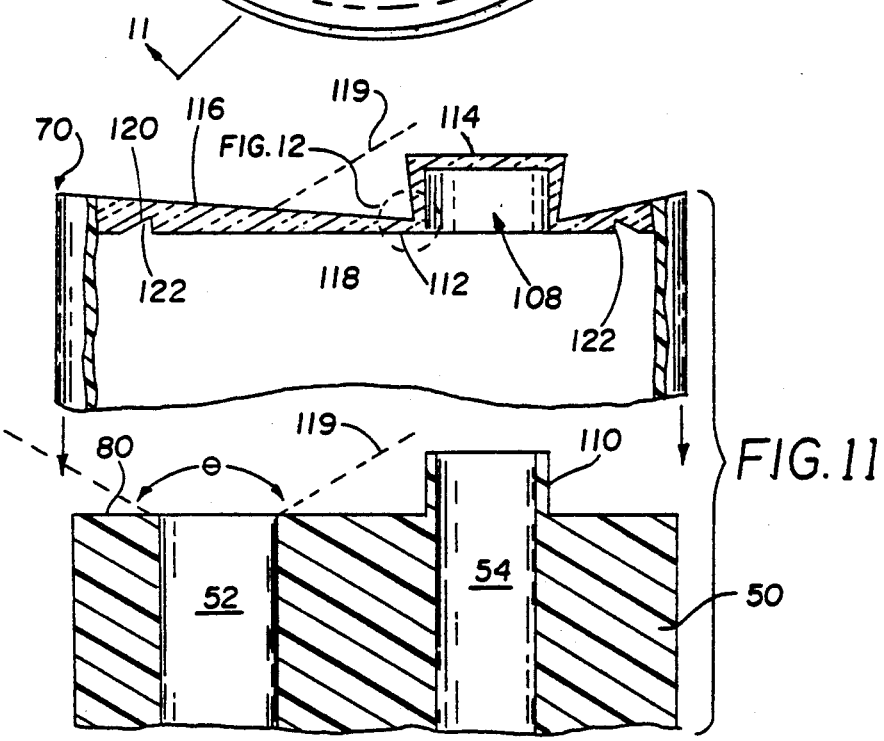
FIG. 11 is an exploded cross-sectional view taken along lines 11—11 of FIG. 10.

FIGS. 10 and 11 illustrate an alternative embodiment of the interfitting region 81 having the image viewer extending from the endoscope 50 and the light source 52 flush with the surface 80 of the endoscope 50. The tip 70 is comprised entirely of transparent material, the shape of the tip being selected to prevent light from spreading from the light guide 52 to the image viewer 54, rather than using an opaque light barrier. The tip 70 includes an opaque recess 108 positioned to mate with projection 110 surrounding the image viewer 54 and extending from the top surface 80 of the endoscope 50. The tip 70 includes a plurality of sharp turns which trap the light and prevent it from extending through the tip from the light source 52 to the image viewer 54.

In the embodiment shown in FIG. 11, a first angle 112 is positioned at the surface of the endoscope, and a second angle 114 is positioned at the top of the recess 108. Any light reflecting within the tip 70 must pass through these two angles, in series, before it reaches the image viewer 54. The shape and position of the angles are selected to trap all light, such that no light is able to successfully reflect internally within the lens material through the two in-series, angled portions.

The lens 70 narrows from the first thickness at point 116 adjacent the light source to a second, narrower thickness at point 118 to further restrict the passage of light within the lens material. This necked-down portion prior to acute angle also traps many internal refractions of light within the tip 70. Reflections from an inside surface of the tip 70 are blocked by the projection 110, providing complete light isolation between the light source member 52 and the image viewer 54.

The distance between the light source 52 and the upper edge of tip 70 over projection 110 is selected to ensure that light does not reenter the tip directly from the light source. The light spreads out of light source 52 along a path 119 at a selected angle $\theta$. The angle $\theta$ varies with the lens 76, but will generally be in the range of 120 degrees. If the projection 110 is too close to the light source, light will enter the tip without first being reflected by an external object. The top of the tip 70 over the projection 110 is spaced and positioned to ensure that the light does not directly enter the tip from the light source and cause glare.

Narrow-necked portions 120 are formed at the edges of the lens 70 by notches 122 in the peripheral region. The use of notches 122 in the peripheral region has been found effective to dampen internal reflections from a side of the lens material and block light entering the edges from the outside to ensure that all light entering the image viewer 54 is from objects positioned generally ahead of and in the viewing field of the image viewer 54.

An advantage of the embodiment of FIGS. 10 and 11 is that the lens material is easily manufacturable, being made of a single member throughout. While having the entire tip 70 of transparent material has presented a problem in the prior art, the particular shape of the tip, together with the combination of the projection 110, prevents light from passing from the light source 52 directly to the image viewer 54, requiring that it be reflected from an objects outside and forward of the endoscope.

Figure 12:
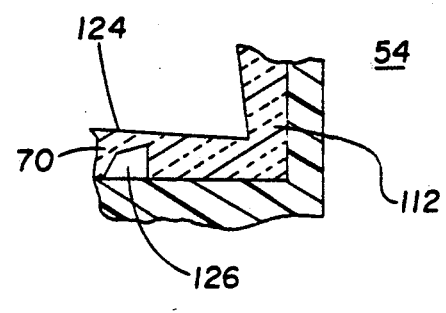
FIG. 12 is an enlarged view of a necked down portion for preventing glare in the tip of an endoscope.

FIG. 12 illustrates a further alternative embodiment of the tip shape between the light source portion 52 and the image viewer 54. According to the embodiment of FIG. 12, a narrow-necked portion 124 is provided in the tip 70 between the light source 52 and image viewer 54 to pinch off light. This narrow-necked portion 124 ensures that no light from internal reflections in the tip 70 reaches the image viewer 54.

The narrow-necked portions 120 and 124 may be formed by machining a notch 126 in the lens, injection molding of the tip 70, or by any other suitable technique to provide a narrow, necked-down portion.

Figure 13:
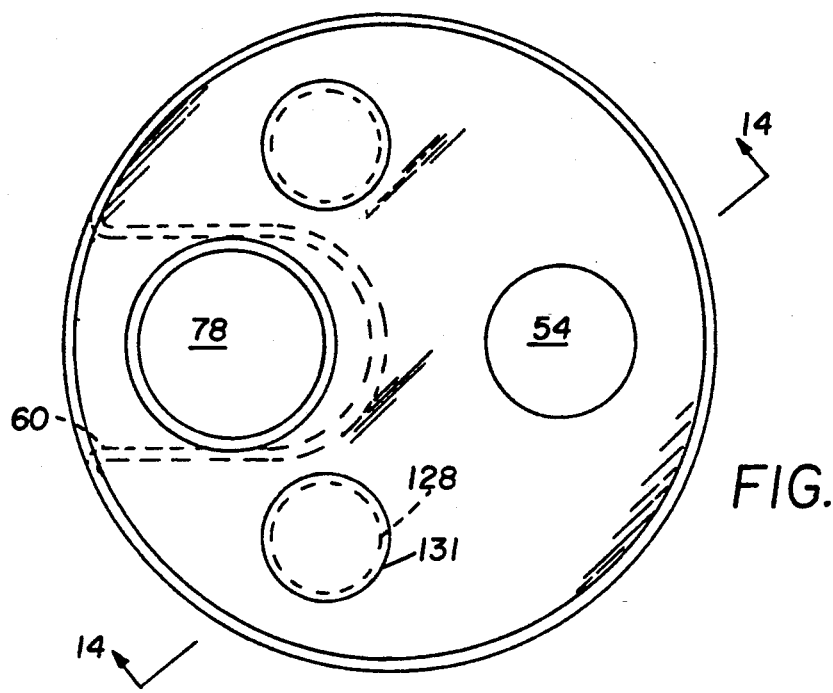
FIG. 13 is an end plan view of an alternative embodiment of a sheath tip and endoscope combination having the light source coupled as an integral portion of the tip and the image viewer flush with the end.
Figure 14:
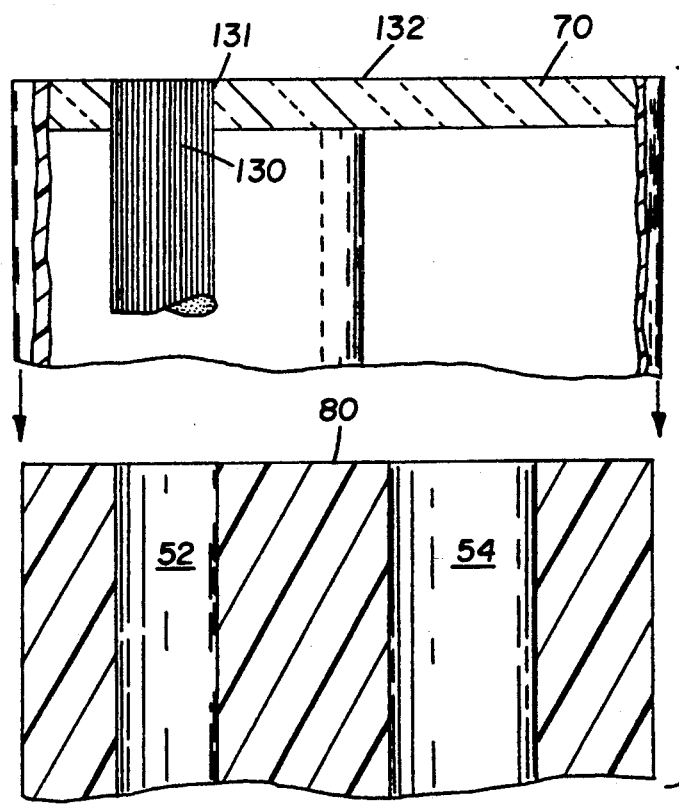
FIG. 14 is an exploded cross-sectional view taken along lines 14—14 of FIG. 13.

FIGS. 13 and 14 illustrate an alternative embodiment having the light source 52 integrally coupled to the tip 70, forming a part of the disposable sheath assembly. The light source 52, such as a light guide 130 of fiber optic cables or clear plastic, is formed in a single step with the tip 70 or later attached. A light-blocking member 131 surrounds the light source 52 along the portion that extends through the tip 70.

Tip 70 is an integral, single-piece tip composed of transparent material. Light exiting from the light source 52 passes through the tip to illuminate objects exterior to the endoscope. The top surface 132 of lens 70 extends generally flat across the entire surface. Both the image viewer and the channel to receive the light source extend flush with a top surface of the endoscope 50. The inside surface of the tip 70 is also flat, except that it effective protrudes as the light guide extends from an inside surface into the endoscope. The light source, surrounded by a light-blocking member 131, extending through the tip, form the interfitting region 81 to prevent unwanted glare in the image viewer. Having a flat outside surface 132 in combination with an integral light source has been found suitable for blocking light between the light source 52 and the image viewer 54. This shape facilitates easy cleaning of the top surface 132.

In a further alternative embodiment of FIG. 14, the shape of the lens 70 is similar to that shown in FIG. 11, the only difference being that the recess 108 extends over a projecting light source 52. The light source is surrounded by a projection, while the image viewer is flush with surface 80. The tip 70 has two angles between the light source 52 and the image viewer 54, just as shown in FIG. 11, with the image viewer and light source configuration reversed. Having the tip flat over the outside surface of the image viewer facilitates cleaning while in the patient's body. While an angle in the tip, and particularly two angles in series, have been found to be effective to block light from the light source 52 to the image viewer 54, a flat upper surface in the tip 70, in combination with either the light source 52 or the image viewer 54 projecting, has been found suitable for blocking light. Of course, one of more opaque light barriers may be provided in the tip 70 of the embodiment of FIGS. 10–13, if desired, along the lines taught in FIGS. 3–7 or 8–9.

Figure 15:
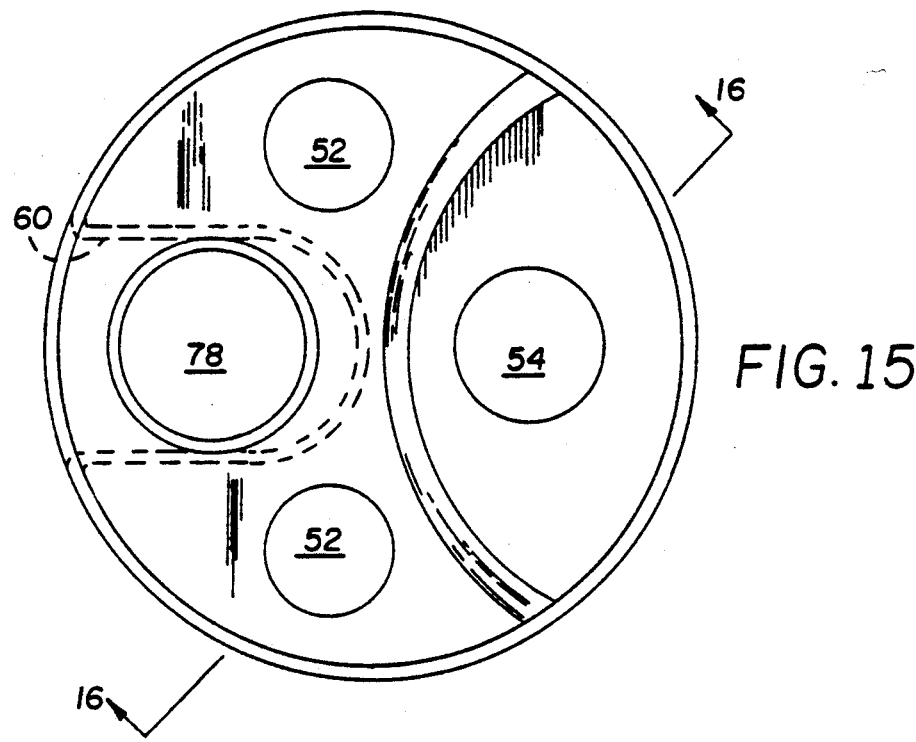
FIG. 15 is an end plan view of a sheath tip and endoscope combination having a raised step between the light source and the image viewer.
Figure 16:
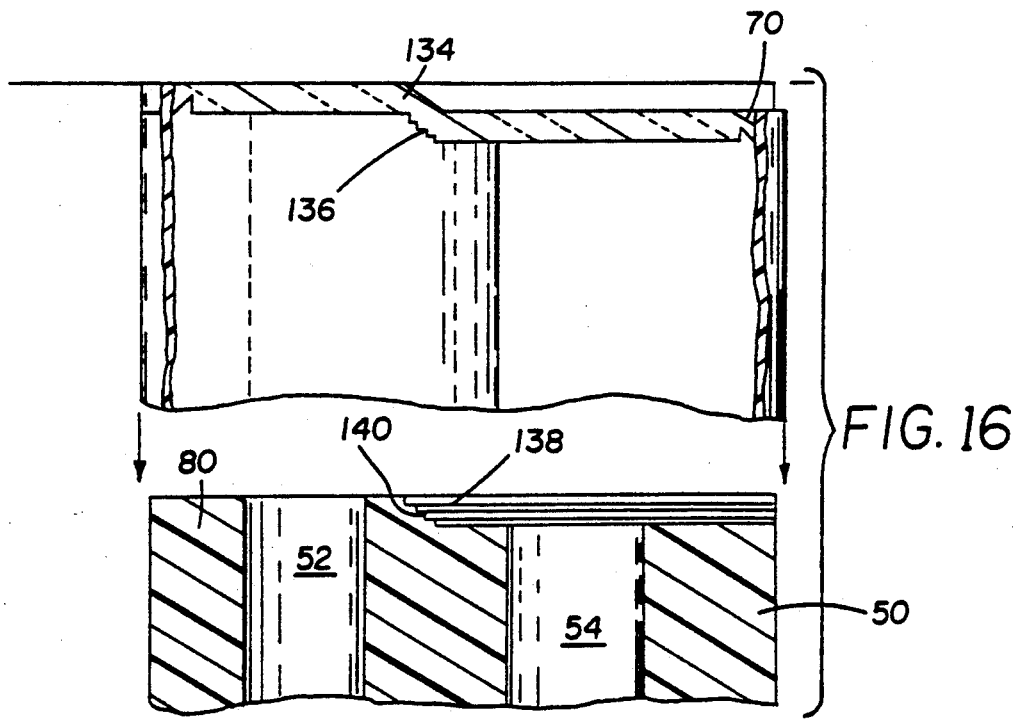
FIG. 16 is an exploded cross-sectional view taken along lines 16—16 of FIG. 15.

FIGS. 15 and 16 illustrate an alternative embodiment of the tip 70, in which the light source 52 and image viewer 54 are separated by a stepped interfitting region 134. The stepped portion 134 extends completely across the tip 70, isolating the light source 52 from the image viewer 54.

The stepped-down interfitting region 134 serves a function identical to the projecting opaque member 100 of the embodiment of FIGS. 8 and 9. The sloped portion 134 blocks internal light reflections within the tip 70, preventing light from passing through the tip from the light source 52 to the image viewer 54. The sawtooth surface 136 on the inside surface of the tip 70 further serves to dampen internal light reflections, and also prevents light reflected from an inside surface of the lens 70 from entering the lenses at the step 134 and entering image viewer 54. The upper surface 80 of the endoscope 50 includes a mating sloped portion 138 with a sawtooth edge 140 to further isolate the image viewer 54 from the light-emitting sources 52. Having the light source 52 and the image viewer 54 at different heights with a stepped portion 134 in the lens 70 ensures that all light entering the image viewer 54 is reflected from objects external of endoscope, and prevents glare from the light within the endoscope. The water and air nozzles may be located in the step 134, if desired, as taught in FIGS. 3–7. The entire tip 70 may be constructed of a single transparent member because light is blocked by the shape of the lens, in conjunction with the shape of the end of the endoscope.

Figure 17:
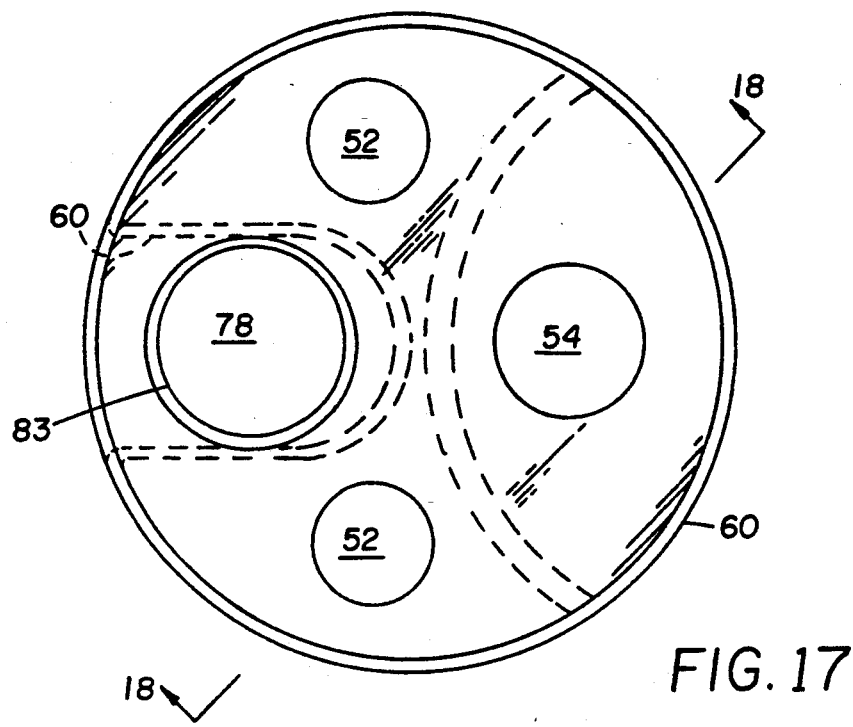
FIG. 17 is an end plan view of a sheath tip and endoscope combination having a projection from the endoscope into the tip.
Figure 18:
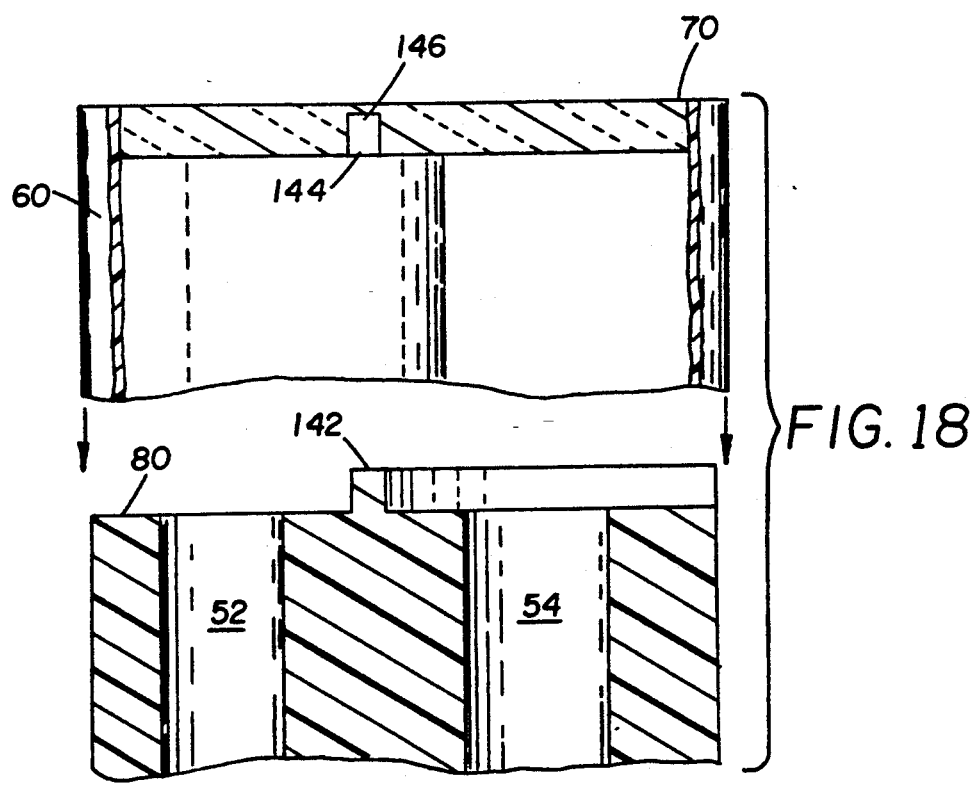
FIG. 18 is an exploded cross-sectional view taken along lines 18—18 of FIG. 17.

FIGS. 17 and 18 illustrate an alternative embodiment having an opaque projection 142 extending as an interfitting region from the endoscope between the light source 52 and the image viewer 54. A recess 144 is positioned in the tip 70 for mating with the projection 142. The projection 142, in combination with the recess 144, is a light barrier to prevent light from passing directly from the light sources 52 to the image viewer 54. The tip 70 is a single, transparent member; however, because the opaque projection 142 extends nearly completely through the tip 70, the light is effectively blocked. The recess 144 extends to a depth sufficient to provide a narrow-necked portion 146 which pinches off light to prevent internal reflections within the tip 70 from reaching the image viewer 54. The projection 142 extending from the surface of the endoscope blocks light from reflections on the inside surface of the tip 70. Thus, light from the light source 52 is prevented from reaching the image viewer 54 unless it passes completely through the tip 70 and is reflected by objects external to the endoscope.

Figure 19:
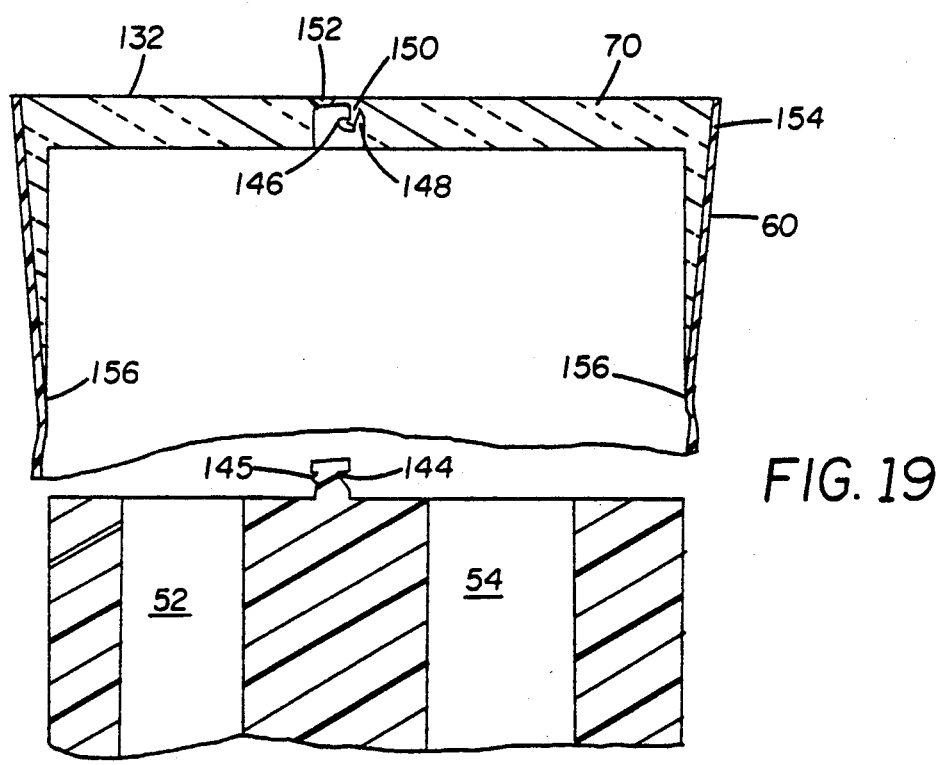
FIG. 19 is an exploded cross-sectional view of a sheath tip and endoscope combination having a locking member to retain the sheath on the endoscope.

FIG. 19 illustrates an alternative embodiment of the projection 142 extending from the end of the endoscope 80, as more fully illustrated in FIGS. 17 and 18. The projection 142 includes a recessed-locking notch 144 located in an upper portion thereof at two or more locations, preferably at each end. The sawtooth surface 145 on the back of projection 142 dampens reflections from the tip 70. The tip 70 includes a locking tab 146 in abutting contact with the notch 144 to lock the tip 70 into abutting contact with the end of the endoscope. The tab 146 is provided with a clearance 148 to permit it to flex back and slide over the projection 142 and catch into the recessed locking notch 144. After the tab 146 has locked into the notch 144, it is not accessible by a user, and thus may not be flexed backward for removal. The tab 146 is coupled to the lens via a narrow-necked, breakaway portion 150 to permit the tab to be broken apart when sufficient force is applied, but to prevent the tab from easily being broken. The tip 70 is removed by exerting sufficient force that the tab 146 is broken, separating the tab from the tip 70. The advantage of providing the breakaway portion is that the tip 70 may not be used a second time, and thus because the sheath and tip are disposable a user may be assured that the tip 70 has not been contaminated by a previous use on another patient. This locking internal tab may be used on any of the previous embodiments of FIGS. 3–18. The tab need not be breakable, but may be user-releasable, if desired.

The tip 70 includes a narrow-necked light trap 152 to prevent internal reflections from within the tip. The use of the narrow-necked light trap 152 may be used in any of the single piece lenses previously described and illustrated in FIGS. 10–18 to further isolate the light source 52 from the image viewer 54.

The side edges 154 of the tip 70 are tapered at an acute angle from the outside surface 132 to a point 156. The tapered side edges 154 prevent reflections from the side entering the image viewer and also block light entering from outside of the tip, at a side region, from entering the endoscope, similar to the function of narrow-necked region 120 of FIG. 11. The side edges of the tip 70 may be similarly tapered in any of the previous embodiments of FIGS. 8–18, if desired, to further isolate the image receiver from light entering a side edge or reflected from a side edge.

Figure 20:
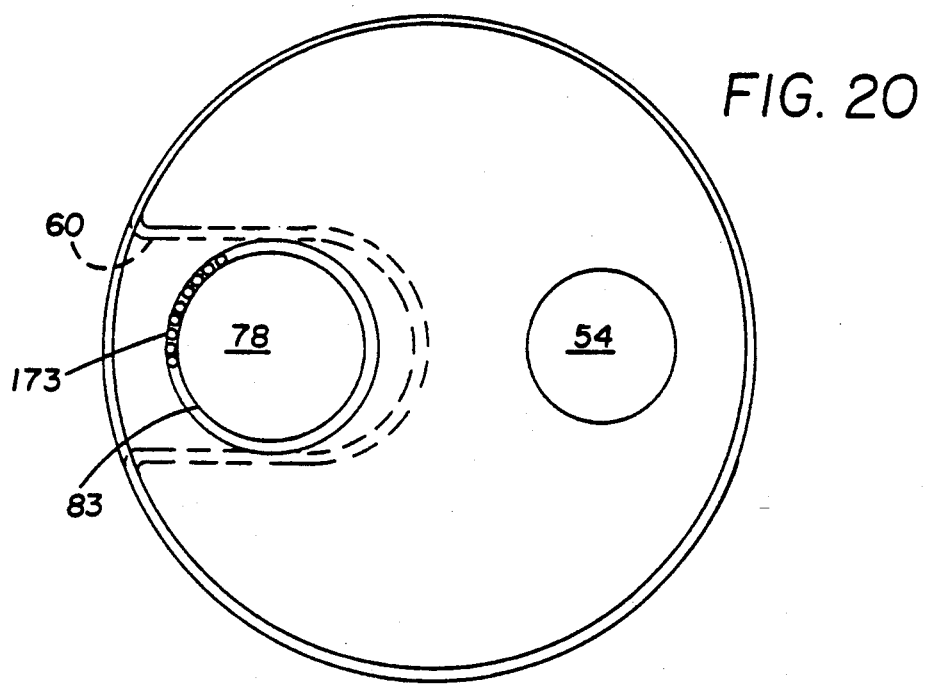
FIG. 20 is an end plan view of an alternative embodiment of the light source combined with the biopsy tube.

FIG. 20 illustrates an alternative embodiment in which the biopsy channel 83 is surrounded by a light source 52. Surrounding a biopsy channel with light transparent material or fiber optic cables is generally known in the field of endoscopes. According to this embodiment of the invention, an interfitting region is formed by the biopsy channel 83, a light blocking member 171 surrounding the biopsy channel 83. The biopsy channel itself is constructed from a transparent material, such as clear plastic, to provide a light guide as part of the light source 52. The biopsy channel can thus be manufactured economically and serve the dual function of providing the light guide for the light source 52 and the wall structure of a biopsy channel 83. Alternatively, fiber optic cables 173 may be positioned around and formed integral with the biopsy channel to provide a high quality light guide. Combining the light source with the biopsy channel 83 take up less space at the end of the endoscope and permits other instruments, such as a ultrasound device, heat treatment device, or the like, to be positioned at the tip.

Figure 21:
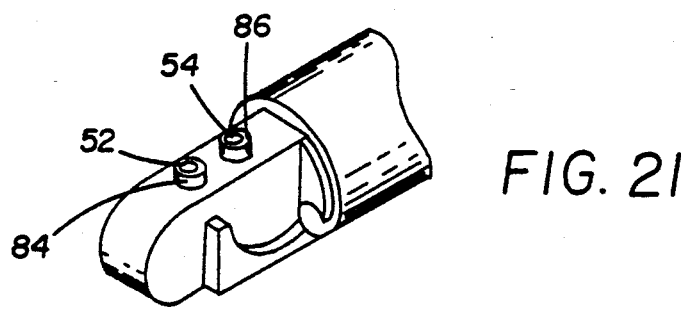
FIG. 21 is an isometric view of a video viewing endoscope having projections around the light source and the image viewer.

FIG. 21 illustrates an endoscope 50 having a side viewing end. The side viewing end includes the appropriate protrusions 84 and 86 around the light source and image viewer, respectively, to provide an interfitting region 81. The tip of the sheath includes recesses to mate with the projections 84 and 86 and is configured to be installed on the side viewing endoscope. The tip having recesses with opaque members is constructed along the lines of the tip of FIGS. 3-7C. Coupling a sheath with a tip to a side viewing endoscope is known generally in the art from U.S. Pat. No. 4,646,722, FIGS. 9-11. If necessary, the tip can be turned into position after it is on the end of the endoscope to properly position a light blocking member interfitting between the light source 52 and the imager viewer 54.

An antiglare tip for the sheath of an endoscope has been described, including alternative embodiments. It will be clear to those of ordinary skill in the art that variations of each of the embodiments described herein, particularly combinations of various features of each, are possible. A biopsy channel and water and air tubings, with their corresponding apertures and nozzles are not required in all embodiments. For example, an industrial endoscope, such as a boroscope, generally requires a light source and an image viewer but does not require a biopsy channel. Cleaning of the surface with water and air may or may not be required in a boroscope. Similarly, some medical applications require water and air but not a biopsy channel, or vice-versa. The sheath and tip may thus be configured to provide the function required by the particular endoscope to which they will be attached. The various combinations are equivalent to structures disclosed herein, and thus fall within the scope of this invention, the invention being defined by the appended claims and not limited to the individual embodiments described herein as to provide an enabling disclosure.

We claim:

1. In an endoscope having a light source and an image viewer at its distal end, a protective sheath covering the distal end of said endoscope, and a tip for said sheath having transparent windows positioned over the light source and the image viewer of said endoscope when said sheath is installed on said endoscope, the improvement comprising an interfitting region positioned between said light source and said image viewer, said interfitting region including a projection from one of said endoscope and said tip and a recess in the other of said tip and endoscope, respectively, mating with said projection, said interfitting region including a light-blocking member that prevents light emitted by said light source from reaching said image viewer, unless it is reflected from objects external to said tip.

2. The improvement of claim 1 wherein said projection is on said tip and said recess is formed in said endoscope, said projection extending from said tip to said endoscope.

3. The improvement of claim 1 wherein said projection is on said endoscope and said recess is formed in said tip, said projection extending from said endoscope to said tip.

4. The improvement of claim 1 wherein said light-blocking member includes an opaque barrier.

5. The improvement of claim 1 wherein said light-blocking member includes a transparent member shaped to block the transmission of light from said light source to said image viewer.

6. The improvement according to claim 4 wherein said opaque barrier extends from an outside surface of said tip, through said tip, and forms said projection from said tip into said endoscope.

7. An apparatus for preventing glare in an endoscope image viewer, comprising:
an endoscope insertion tube having a light source and an image viewer, an end of said endoscope including an opaque projection extending between said light source and said image viewer;
a sheath coupled to said endoscope; and
a tip coupled to a distal end of said sheath, said tip including transparent members positioned over said light source and said image viewer, a recess positioned to mate with said projection of said endoscope end, and opaque portions extending around the periphery of said transparent members to block light from passing directly from said light source to said image viewer.

8. The apparatus according to claim 7 wherein said tip includes a single-piece opaque member having a plurality of apertures and transparent members mounted within said apertures, said transparent members being thinner than said opaque member to form said recesses.

9. The apparatus according to claim 8 wherein said transparent members are mounted flush with an outside surface of said single-piece opaque member to provide a flat outside surface region.

10. The improvement according to claim 9, further including a raised step in said opaque member, said raised step being adjacent said image viewer and having an aperture therein sized to provide a nozzle positioned to direct a water spray across said outside surface to clean the transparent member positioned over said image viewer.

11. A sheath having an antiglare tip for coupling to an endoscope, comprising:
a sheath adapted to be coupled to an endoscope; and
a tip coupled to a distal end of said sheath, said tip including a transparent member means adapted to be positioned over a light source of said endoscope and an image viewer of said endoscope, the transparent member means including a transparent member that is recessed and adapted to mate with a projection of said endoscope to prevent light from passing directly through said transparent member from said light source to said image viewer.

12. The sheath according to claim 11 wherein said recess is positioned to extend over said light source and mate with said projection extending rom the end of said endoscope to ensure that light exiting from said light source does not pass through said transparent member means to said image viewer.

13. The sheath according to claim 11 wherein said recess is positioned to extend over said image viewer and mate with said projection extending from the end of said endoscope to ensure that light exiting from said light source does not pass through said transparent member means from said light source to said image viewer.

14. The sheath according to claim 13 wherein said tip includes a single-piece opaque member having a plurality of apertures therethrough and said transparent member means includes a plurality of transparent members mounted in said apertures, said transparent members being thinner than said opaque member to form said recesses.

15. The combination according to claim 14 wherein said transparent members are mounted flush with an outside surface of said single-piece opaque member to provide a flat outside surface region.

16. The sheath according to claim 11 wherein said transparent member means includes a single transparent member extending over said light source and said image viewer.

17. The sheath according to claim 16 wherein said transparent member includes a narrow neck portion adjacent a said portion of said tip to reduce the glare and to trap light and prevent it from passing from one portion of said transparent member to a second portion of said transparent member.

18. The sheath according to claim 16 wherein said transparent member includes a narrow neck portion between a portion adapted to extend over said light source and a portion adapted to extend over said image viewer to aid in blocking light traveling through said transparent member from said light source to said image viewer.

19. The sheath according to claim 11 wherein said transparent member means includes an opaque member positioned within said tip between said light source and said image viewer.

20. An endoscope and antiglare tip coupled to the sheath combination, comprising:
    an endoscope insertion tube having a light source and an image viewer, an end of said endoscope including an opaque projection extending from said end and positioned between said light source and said image viewer;
    a sheath coupled to said endoscope; and
    a tip coupled to a distal end of said sheath, said tip including transparent members positioned over said light source and said image viewer, a recess in said tip positioned to mate with said projection of said endoscope, said projection extending into said recess to prevent light from passing directly from said light source to said image viewer.

21. The combination according to claim 20 wherein said projection includes a recessed locking notch and said tip includes a locking tab in abutting contact with said notch to lock an opaque portion of said tip into abutting contact with the end of said endoscope.

22. The combination according to claim 21 wherein said locking tab includes a narrow-necked, breakaway portion which breaks apart from said tip under force to permit said tip to be removed from said endoscope but prevents said tip from being used a second time.

23. The combination according to claim 20 wherein said tip further includes a projecting opaque member extending from said tip into a mating recess of said endoscope and positioned between respective transparent members to block light between said light source and said image viewer.

24. The combination according to claim 20 wherein said tip includes a single-piece opaque member having a plurality of transparent members mounted in apertures therein, said transparent members being thinner than said opaque member to form said recesses.

25. A method for providing an antiglare tip for an endoscope, comprising the steps of:
    providing a single-piece opaque member;
    forming apertures in said opaque member;
    inserting transparent members into said apertures, said transparent member being thinner than said opaque member and mounted flush at an outside surface to form recesses on an inside surface of said opaque member; and
    attaching said opaque member to a sheath to provide a sheath having an antiglare tip.

26. The method according to claim 25, further including the step of:
    coupling said sheath to an endoscope having projections to mate with said recesses, said projections extending into said recesses.

27. The method according to claim 25 wherein said apertures are cylindrical and include a first diameter region and a second diameter region, said second diameter region being larger in diameter than said first diameter region to provide a shoulder region extending perpendicular to the axial direction of said aperture, said shoulder region being adapted to receive said transparent members to ensure that said transparent members are mounted flush at their edges with an outside surface of said opaque member when abutting against said shoulder region.

28. The method according to claim 27 wherein said step of inserting transparent members include:
    pressing said transparent members into said apertures with a mechanical assembly until said transparent members abut against said shoulder.

29. The method according to claim 27 wherein said step of inserting transparent members includes:
    manually pressing said transparent members into said apertures.

30. The method according to claim 25 wherein said step of forming said apertures includes:
    machining the desired apertures into said opaque member.

31. The method according to claim 25 wherein said step of forming said apertures includes:
    injection molding a single-piece opaque member, said mold having a shape to provide said apertures.

* * * * *

UNITED STATES PATENT AND TRADEMARK OFFICE
CERTIFICATE OF CORRECTION

PATENT NO. : 5,193,525

DATED : March 16, 1993

INVENTOR(S) : Fred E. Silverstein et al.

It is certified that error appears in the above-identified patent and that said Letters Patent is hereby corrected as shown below:

In column 14, claim 12, line 54, please delete "rom" and substitute therefor --from--.

Signed and Sealed this

Thirtieth Day of November, 1993

Attest:

BRUCE LEHMAN

Attesting Officer    Commissioner of Patents and Trademarks